(12) United States Patent
Seipel et al.

(10) Patent No.: US 8,632,561 B2
(45) Date of Patent: Jan. 21, 2014

(54) SURGICAL CUTTING DEVICE AND METHOD FOR PERFORMING SURGERY

(75) Inventors: Pete Seipel, Scottsdale, AZ (US); David Hunn, Mesa, AZ (US)

(73) Assignee: Pete Seipel, Scottsdale, AZ (US)

( * ) Notice: Subject to any disclaimer, the term of this patent is extended or adjusted under 35 U.S.C. 154(b) by 237 days.

(21) Appl. No.: 12/836,420

(22) Filed: Jul. 14, 2010

(65) Prior Publication Data

US 2011/0087260 A1 Apr. 14, 2011

Related U.S. Application Data

(60) Provisional application No. 61/225,835, filed on Jul. 15, 2009.

(51) Int. Cl.
*A61B 17/32* (2006.01)
(52) U.S. Cl.
USPC .......................................... 606/180; 606/170

(58) Field of Classification Search
USPC ............. 606/79, 159, 170, 180; 600/564, 568
See application file for complete search history.

(56) References Cited

U.S. PATENT DOCUMENTS 7,276,074 B2 * 10/2007 Adams et al. ................. 606/170
8,070,762 B2 * 12/2011 Escudero et al. ............. 606/159

* cited by examiner

*Primary Examiner* — Thomas McEvoy
*Assistant Examiner* — Sarah W Aleman
(74) *Attorney, Agent, or Firm* — Merchant & Gould P.C.

(57) ABSTRACT

A surgical cutting device and method for performing surgery using such is provided. The surgical device includes a handpiece or other, a stationary outer cannula connected to the base, a rotatable inner cannula connected to the base, an inner elongated shaft member connected to a distal interior surface of the lumen of the outer cannula, and a tissue cutting opening. The inner cannula includes a plurality of blades that interact with a plurality of ridges on the inner elongated shaft upon rotation of the inner cannula facilitating maceration of tissue within the lumen to prevent clogging of the device.

17 Claims, 4 Drawing Sheets

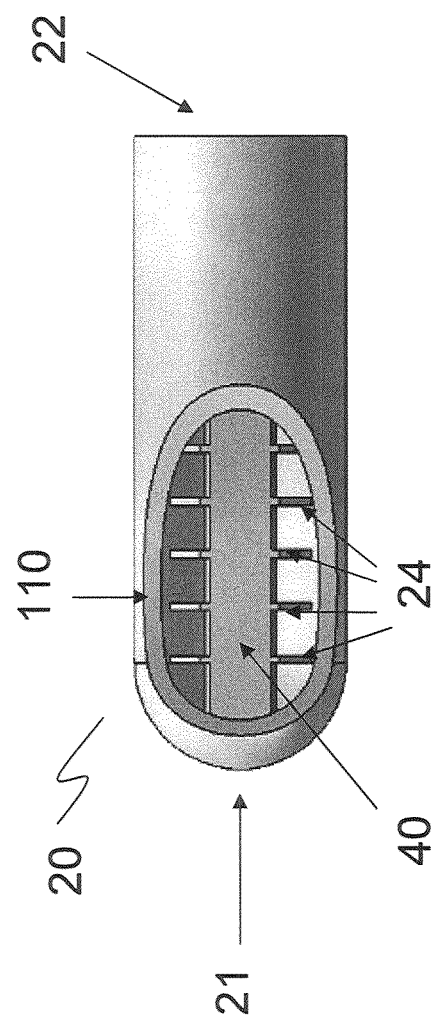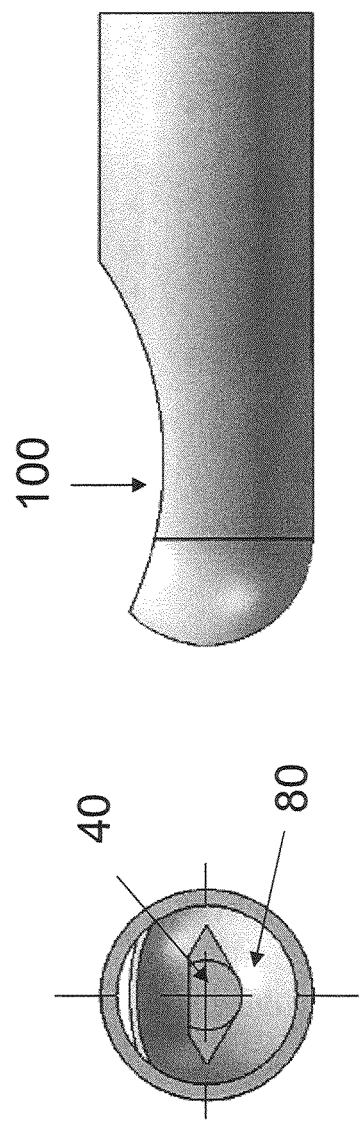

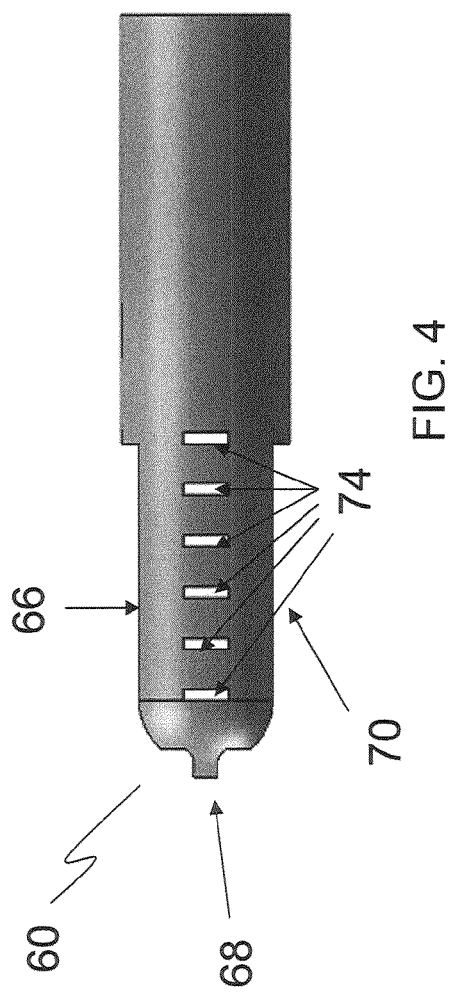
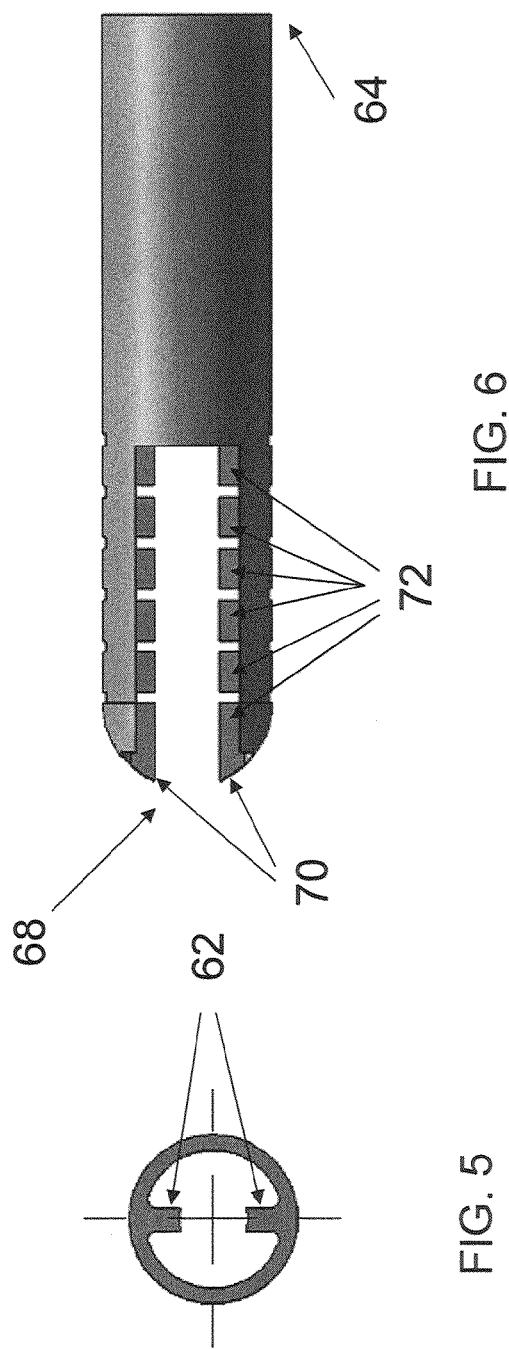
FIG. 4
FIG. 5
FIG. 6

SURGICAL CUTTING DEVICE AND METHOD FOR PERFORMING SURGERY

CROSS REFERENCE TO RELATED APPLICATION(S)

This application claims the benefit of priority under 35 U.S.C. §119(e) of U.S. Ser. No. 61/225,835, filed Jul. 15, 2009, the entire content of which is incorporated herein by reference.

BACKGROUND OF THE INVENTION

1. Field of the Invention

The present disclosure relates generally to medical devices and more specifically to surgical cutting devices and methods for performing surgery using such devices.

2. Background Information

Many types of surgical procedures are routinely performed that require use of surgical cutting devices which enable removal of hard or soft tissue from the body. For example, arthroscopic surgery is a procedure, often minimally invasive, in which an examination of interior of a joint is performed using an arthroscope, with which a surgical device, such as an arthroscopic catheter, may be employed for treatment. Arthroscopic procedures can be performed either to evaluate or to treat many orthopedic conditions including torn floating cartilage, torn surface cartilage, anterior cruciate ligament (ACL) reconstruction, and trimming damaged cartilage and/or bone.

Typical catheter-based surgical cutting instruments include an outer cannula or sleeve with a cutting aperture and an inner cannula or tube rotatably mounted within the outer cannula with a cutting or grinding surface at the tip, such as a screw or burr. Examples of instruments of this type are disclosed in U.S. Pat. No. 4,368,734, U.S. Pat. No. 3,618,611, U.S. Pat. No. 5,217,479 and U.S. Pat. No. 5,931,848.

Two major disadvantages of such devices is their inability to (1) macerate or grind cut tissue that is drawn into the inner lumen of the device to an extent sufficient to avoid clogging of the lumen and allow aspiration of the tissue from the device, and (2) be used to treat more than one tissue type. In the latter respect, an arthroscopic procedure may entail removal of both hard tissue and cartilage. Many devices whose cutting tips are aggressive enough to remove bone are too aggressive to be used on cartilage without risk of damaging tissue around the treatment site. Yet having a device which can be used with one such tissue but not the other requires deployment of multiple devices over the course of a procedure, adding to its length, cost and complexity.

Accordingly, there has been a need for an improved surgical cutting device that has a reduced blockage profile and is capable of treating both bone and cartilage.

SUMMARY OF THE INVENTION

The present invention provides a surgical cutting device that includes a proximal base and a catheter comprising at least one lumen in which a cutting tip is disposed at its distal end. The cutting tip comprises an outer cannula having at least one lumen therethrough. An inner elongated shaft is secured to the outer cannula at its distal end, and an inner cannula is rotatably disposed between the elongated shaft and the outer cannula. The outer cannula includes a tissue cutting opening at the distal end of the outer cannula.

In one embodiment, the inner elongated shaft extends from the distal tip along the longitudinal axis of the outer cannula toward the proximal end of the cannula and includes a plurality of ridges or ribs extending radially from the shaft. The inner cannula rotatably disposed between the outer cannula and the inner shaft includes a cutting edge which interacts with the tissue cutting opening along with a plurality of blades which interact with the ridges or ribs of the inner shaft when the inner cannula is rotated. Such rotation facilitate cutting of the tissue and its maceration during aspiration to assist in its removal without clogging of the inner lumen.

The invention further provides a method of performing a surgical procedure, such as arthroscopic surgery, using the device of the present invention. The method includes inserting a surgical cutting device as described herein, into a tissue or cavity within the tissue, actuating the surgical cutting device to provide rotation of the inner cannula, and applying a vacuum to the lumen of the surgical device to facilitate aspiration of the tissue from the opening at the distal end of the outer cannula longitudinally along the lumen toward the proximal end of the outer cannula.

BRIEF DESCRIPTION OF THE DRAWINGS

The features and inventive aspects of the present invention will become more apparent upon reading the following detailed description, claims, and drawings, of which the following is a brief description:

FIG. 1 is a top view of an embodiment of a surgical cutting device showing the distal tip of an outer cannula;

FIG. 2 is a cross-sectional view of the embodiment of FIG. 1 showing the outer cannula of a surgical cutting device;

FIG. 3 is a side view of the embodiment of FIG. 1 showing the outer cannula of a surgical cutting device;

FIG. 4 is a top view of an embodiment of a surgical cutting device showing the distal tip of an inner cannula;

FIG. 5 is a cross-sectional view of the embodiment of FIG. 4 showing the inner cannula of a surgical cutting device;

FIG. 6 is a side view of the embodiment of FIG. 4 showing the inner cannula of a surgical cutting device;

DETAILED DESCRIPTION OF THE INVENTION

Figure 7:
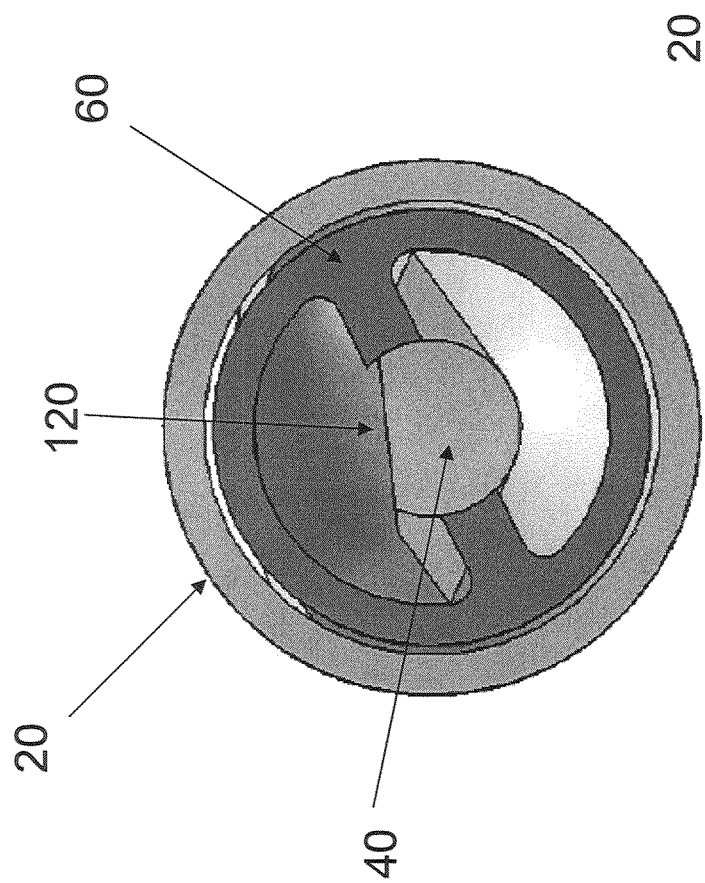
FIG. 7 is a cross-sectional view of an embodiment of a surgical cutting device showing the outer cannula of FIGS. 1-3 in assembly with the inner cannula of FIGS. 4-6.

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

Referring to FIGS. 1-8, an embodiment of the distal cutting tip of a surgical cutting device 10 (FIG. 8) in accordance with the present invention is shown. The surgical cutting device includes a base (not shown), a catheter having at least one longitudinal lumen disposed between proximal and distal ends, an outer cannula 20 that is non-rotatably secured to or disposed within the distal end of the catheter, an inner elongated shaft 40 secured to the outer cannula 20 at its distal end 21, and an inner cannula 60 that is rotatably disposed between the elongated shaft 40 and the outer cannula 20.

In various embodiments, the base of surgical cutting device 10 may comprise a handpiece. The handpiece acts as a base for engaging the surgical cutting device and provides functionality for rotating inner cannula 60, while maintaining outer cannula 20 stationary with reference to the base. A variety of handpieces may be suitably adapted for use with the surgical cutting tip as will be recognized by one of skill in the art. Typically, the handpiece will be provided with a rotational drive member for interacting with inner cannula 60 to provide rotational force to the inner cannula 60 and rotate the component within the outer cannula 20 upon actuation of the handpiece. The handpiece may also be adapted to oscillate the inner cannula 60 in embodiments were oscillation is suitable. Other additional features of the handpiece may include one or more handpiece guides to facilitate the alignment of the handpiece with other medical equipment, such as an endoscope, or means for providing a vacuum to aspirate macerated tissue.

Connected to the handpiece is inner cannula 60 disposed within outer cannula 20. The proximal end 22 of the outer cannula 20 is connected to or disposed within a catheter so it is stationary with respect to inner cannula 60, which is rotatably connected to the handpiece at its proximal end. As exemplified in the embodiment shown in FIG. 5, inner cannula 60 typically includes features for releasably interacting with the rotational drive of the handpiece, such as notch features 62. One of skill in the art would understand that a number of alternative embodiments of features 62 are possible depending in part on the design of the rotational drive of the handpiece. Alternatively, inner cannula 60 may be permanently fused to the rotational drive of the handpiece. Likewise, outer cannula 20 may be either permanently fused to the catheter or may include features that allow it to be removable, such as threads, or other removably interlocking feature known in the art.

The outer cannula includes a distal end 21 defining the tip of the surgical cutting device. The outer cannula 20 is hollow and defines an inner lumen 80, best shown in FIG. 2. Within lumen 80, is an inner elongated shaft 40 that that is secured to the inner surface of the outer cannula 20 at the distal tip 21 which extends from the distal tip 21 along the longitudinal axis of the outer cannula 20 toward the proximal end 22 of the cannula. The outer cannula 20 further includes a tissue cutting opening 100 at the distal end 21 of the outer cannula which provides cutting edge or surface 110.

As best shown in FIGS. 4-6, inner cannula 60 includes a proximal end 64 rotatably connected to the handpiece and a distal end 68. At the distal region of the inner cannula 60, at least one elongated member 70 extends along the longitudinal axis of the outer cannula and for at least the length of the tissue cutting opening 100. While the embodiment provided in the figures includes 2 elongated members 70, embodiments are contemplated wherein only one elongated member 70 is utilized, or where 3 or more elongated members 70 are utilized. Each elongated member 70 includes a cutting edge 66 which interacts with cutting edge 110 of the tissue cutting opening 100 in the outer cannula 20. Upon rotation of the inner cannula 60, cutting edge 66 interacts with cutting edge 110 to cut tissue and draw the cut tissue into lumen 80. As is evident to one of skill in the art, the cutting edges are dependent upon the direction of rotation of inner cannula 60, examples include forward, reverse or oscillate. Accordingly, while reference is made to cutting edges present upon clockwise rotation of inner cannula 60 with regard to the view of FIG. 7, cutting edges are intended to include those edges that serve the same function upon counterclockwise rotation of inner cannula 60.

As shown in the embodiment of FIG. 3, the tissue cutting opening 100 may be arcuately shaped to define an elliptically shaped opening. The opening provides cutting edge or surface 110 and allows cut tissue to enter the lumen 80 and become macerated by interaction of features of inner cannula 60 and inner elongated shaft 40 as discussed further below. While the figures show an embodiment in which tissue cutting opening 100 is generally elliptical, one of skill in the art would realized that the opening may be a variety of shapes, such as circular, square, rectangular, triangular, and the like. Opening 100 may be of any shape that allows contact of cutting edges 110 and 66 with tissue. Accordingly, cutting edge 110, may be of any suitable shape determined by the shape of opening 100, such as linear, curvilinear, arcuate, or the like.

As shown best in FIGS. 4 and 6, elongated members 70 at the distal region of inner cannula 60 may include additional features that facilitate maceration of tissue once the tissue enters lumen 80. Each elongated member 70 further includes a plurality of spaced blades 72. A space or gap is provided between each blade 72 which allows the blades to interdigitate or interact with ridges or ribs, blades 24 spaced along elongated shaft 40. It will be understood by one of skill in the art that features 24 may be sharpened to act as blades. In various embodiments, the number of blades 72 spaced along the elongated member 70 is any number more that one, accompanied by a corresponding number of ridges 24. For example, 2, 3, 4, 5, 6, 7, 8, 9, 10 or more blades may be utilized along with a corresponding number of ridges. While the figures depict an embodiment in which the blades are rectangular and define spaces that are also rectangular, embodiments are contemplated in which the blades are any other geometric shape, such as square, triangular, trapezoidal, rhombozoidal, circular, or the like, with the ridges being the shape of the space or gap dictated by the shape of the blade.

To help facilitate continuous suction and maceration of tissue within lumen 80, elongated members 70 may further include a plurality of openings defined by slits 74 as shown in FIG. 4. Slits 74 allow continuous suction and maceration of tissue by providing an opening in which tissue enters the spaces between blades 72 by ridges 24 can pass to facilitate continuous suction and finer grinding of tissue within lumen 80. Slits 74 are positioned in the spaces or gaps between the blades 72 and radially traverse portions of the elongated member, and are sized to accommodate ribs 24. Generally, the number of slits 74 corresponds with the number of spaces or gaps, however, a slit 74 is not required to be positioned in every space or gap created by positioning of blades 72.

Ridges or ribs 24 are spaced along the length of inner elongated shaft 40 and extend radially therefrom. Ribs 24 may be spaced around the entire circumference of inner elongated shaft 40 and may be of any appropriate shape. As best shown in FIGS. 1 and 2, in one embodiment, triangular shaped ridges are provided in 2 opposing rows that extend longitudinally from distal end 21 toward the proximate end 22 and are positioned or extend perpendicular to the latitudinal axis of opening 110. However, various embodiments are contemplated in which varying numbers of rows are utilized, such as 1, 2, 3, 4, 5, 6, 7 or more rows. Additionally, the ridges may be positioned on inner elongated shaft 40 in a variety of alternative configurations, so long as inner cannula 60 may be inserted over inner elongated shaft 40 during assembly of the device and macerated tissue is allowed to flow from the distal end 21 toward the proximal end 22 upon applying a vacuum or suction to the proximal end of the lumen 80. Further, ridges may be positioned or extend in any orientation relative to the latitudinal axis of opening 110, such as parallel with the latitudinal axis.

Inner elongated shaft 40 may have a variety of cross-sectional geometries. In the embodiment shown in FIGS. 2 and 7 the cross-sectional geometry is a partial circle having a flat portion 120 which is on the side of the shaft adjacent opening 110. While the cross-sectional geometry of the shaft is generally circular or circular with flat portion 120, other shapes are envisioned. Additionally, the partial circle portion of shaft 40 may be anywhere from a full circle to a half circle and positioned on shaft 40 in any orientation with respect to opening 110.

Figure 8:
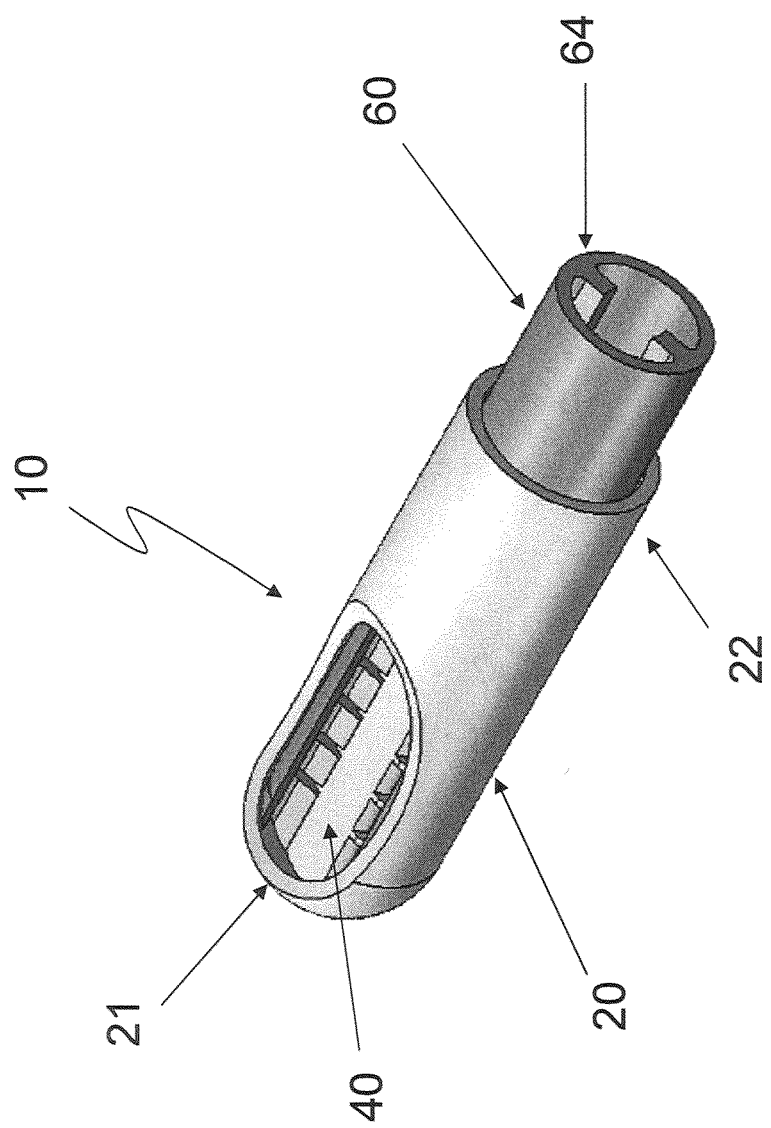
FIG. 8 is a perspective view of an embodiment of the cutting tip of a surgical cutting device.

As best depicted in FIGS. 7 and 8, inner cannula 60, is rotatably disposed between outer cannula 20 and elongated inner shaft 40. During operation of the device, upon actuation, inner cannula 60 is rotated by rotational forces generated by the connected base, e.g., a rotational drive shaft. Tissue is initially cut by interaction of cutting edges 66 and 110 and pulled into lumen 80 via opening 100. As inner cannula 60 rotates, blades 72 and ridges 24 are positioned such that rotation facilitates interaction between the components to macerate the tissue. A vacuum applied to the proximal region of lumen 80 facilitates aspiration of the tissue and further maceration of the tissue as it travels from the distal end 21 toward the proximal end 22 thus preventing clogging of lumen 80.

The invention further provides a method of performing a surgical procedure, such as arthroscopic surgery, using the surgical cutting device described herein. The method includes inserting the surgical cutting device as described herein, into a tissue or cavity within the tissue, actuating the surgical cutting device to provide rotation of inner cannula 40, and applying a vacuum to lumen 80 of the surgical device to facilitate aspiration of macerated tissue from opening 110 at the proximal end 21 of outer cannula 20 longitudinally along lumen 80 toward the distal end 22 of the outer cannula.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. Moreover, the foregoing embodiments are illustrative, and no single feature or element is essential to all possible combinations that may be claimed in this or a later application.

What is claimed is:

1. A surgical cutting device comprising:
   a) a catheter defining at least one longitudinal lumen, wherein the catheter has a distal end and a proximal end non-rotatably securable to a base;
   b) a cutting tip formed integrally with or disposed within the distal end of the catheter, comprising an outer cannula defining a lumen having a longitudinal axis between proximal and distal ends, an inner surface, and an opening at the distal end for receiving tissue, wherein the opening has a length extending along the longitudinal axis and a cutting edge for facilitating cutting of tissue;
   c) an inner elongated shaft member secured to the inner surface of the outer cannula at the distal end and extending toward the proximal end along the longitudinal axis, wherein the inner elongated shaft member further comprises a plurality of ridges extending radially from the inner elongated shaft member; and
   d) an inner cannula securable to a base and rotatably disposed within the lumen of the outer cannula and radially positioned between the inner surface of the outer cannula and the inner elongated shaft member, wherein the inner cannula has proximal and distal ends and at least one elongated cannula member extending along the longitudinal axis of the outer cannula and for at least the length of the opening, wherein the elongated cannula member further comprises: an edge positioned to rotatably interact with the cutting edge of the opening, and a plurality of interspaced blades positioned to rotatably receive the plurality of ridges extending radially from the inner elongated shaft member to facilitate the cutting of tissue, wherein the inner cannula rotates with respect to the outer cannula and the inner elongated shaft member.

2. The surgical cutting device of claim 1, wherein the elongated cannula member extending along the longitudinal axis of the outer cannula further comprises a plurality of openings defined by slits, radially traversing portions of the elongated cannula member, and sized to receive the plurality of ridges extending radially from the inner elongated shaft member.

3. The surgical cutting device of claim 2, wherein the plurality of ridges extending radially from the inner elongated shaft member, extend radially around less than the entire circumference of the inner elongated shaft member.

4. The surgical cutting device of claim 2, wherein the plurality of ridges extending radially from the inner elongated shaft member extend radially and intermittently around the circumference of the inner elongated shaft member.

5. The surgical cutting device of claim 4, wherein the plurality of ridges extending radially from the inner elongated shaft member form at least one row extending along the longitudinal axis of the outer cannula.

6. The surgical cutting device of claim 5, wherein the plurality of ridges extending radially from the inner elongated shaft member form two rows opposite one another.

7. The surgical cutting device of claim 6, wherein the two rows are perpendicular to the opening.

8. The surgical cutting device of claim 7, wherein the proximal end of the inner cannula further comprises more than one elongated cannula member.

9. The surgical cutting device of claim 8, wherein the plurality of slits of each elongated cannula member are oriented opposite each other along the longitudinal axis.

10. The surgical cutting device of claim 1, wherein a vacuum is applied to the lumen of the outer cannula through the base to facilitate movement of tissue from the distal end of the outer cannula to the proximal end of the outer cannula.

11. The surgical cutting device of claim 1, wherein the edge of the elongated cannula member positioned to rotatably interact with the cutting edge of the opening further comprises serrations or cutting teeth for facilitating cutting of tissue.

12. The surgical cutting device of claim 1, wherein a cross-sectional shape of the inner elongated shaft member is circular.

13. The surgical cutting device of claim 1, wherein the cross-sectional shape of the inner elongated shaft member is a partial circle having a flat portion.

14. The surgical cutting device of claim 13, wherein the partial circle is between a half circle and a full circle.

15. The surgical cutting device of claim 14, wherein the flat portion is adjacent the opening.

16. The surgical cutting device of claim 1, wherein the opening is circular or elliptical.

17. The surgical cutting device of claim 1, wherein the edge of the opening of the outer cannula for facilitating cutting of tissue is linear, curvilinear or arcuate.

* * * * *